United States Patent [19]

Chastain et al.

[11] Patent Number: 5,543,435
[45] Date of Patent: Aug. 6, 1996

[54] USING LIMONEN-10-OL TO KILL BACTERIA, YEAST, AND FUNGI

[75] Inventors: Doyle E. Chastain, 137 Birch St., Titusville, Fla. 32780; W. Eugene Sanders, Jr.; Christine C. Sanders, both of Omaha, Nebr.

[73] Assignee: Doyle E. Chastain, Titusville, Fla.

[21] Appl. No.: 224,302

[22] Filed: Apr. 7, 1994

[51] Int. Cl.[6] .................... A01N 31/00; A61K 31/045
[52] U.S. Cl. ............................................... 514/729
[58] Field of Search ............................... 514/729

[56] References Cited

U.S. PATENT DOCUMENTS 5,294,645  3/1996  Chastain et al. .................. 514/729

OTHER PUBLICATIONS

Sakai et al, C.A. vol. 100 (1984) 100:192085j.

Primary Examiner—Allen J. Robinson
Attorney, Agent, or Firm—Arthur G. Yeager; Earl L. Tyner

[57] ABSTRACT

Bacteria, fungi, or yeast are treated in their habitat with lethal concentrations of limonen-10-ol.

4 Claims, No Drawings

USING LIMONEN-10-OL TO KILL BACTERIA, YEAST, AND FUNGI

TECHNICAL FIELD

The object of this invention is to demonstrate a method of using LIMONEN-10-OL to kill bacteria, yeast, and fungi.

BACKGROUND OF THE INVENTION (1) Field of the invention

During the study of limonene as a hand cleaner, it was found that limonene can be made bactericidal and fungicidal as was illustrated by the applicants in U.S. Pat. Nos. 5,153,229 and 5,229,425. A review of the literature showed that oxidized limonene contains several oxidation products including cis and trans-carveol, trans-p-menth-8-ene-1,2-diol, limonene 1,2-epoxide, limonene 8,9-epoxide, cis and trans-p-mentha-2,8-dien-1-ol, and perillyl alcohol, as was outlined by Blumann in Chemical Abstracts, Volume 63, 1965, on page 1819. The applicants decided to study other monocyclic monoterpenes for antimicrobial activity. Because limonene is not bactericidal and because the chemical structures of limonene and limonen-10-ol are identical except for a hydroxyl group replacing a hydrogen atom at carbon 10, the applicants were surprised to find that limonen-10-ol is bactericidal and fungicidal. A review showed that all the monocyclic monoterpenes that are known to be antimicrobial have an oxygen molecule or hydroxyl group replacing a hydrogen atom at carbons 2, 3, 4, or 8. Prior to the discovery by the applicants that perillyl alcohol is bactericidal, as demonstrated in U.S. Pat. No. 5,110,832, and menth-1-en-9-ol is bactericidal and fungicidal as outlined in U.S. Pat. No. 5,294,645 no monocyclic monoterpene with an oxygen or a hydroxyl group at carbon 7, 9 or 10 was recognized as having antimicrobial activity. After the applicants discovered that perillyl alcohol is bactericidal, the applicants decided to study limonen-10-ol for antimicrobial activity and were pleasantly surprised to find that limonen-10-ol kills bacteria, yeast, and fungi in bactericidal and fungicidal concentrations.

The chemical structures of limonene and limonen-10-ol follow below.

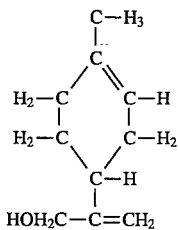

Limonen-10-ol

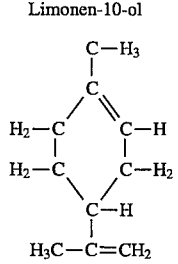

Limonene

Because limonene is not bactericidal nor fungicidal and because the chemical structures of limonene and limonen-10-ol are identical except for a hydroxyl group replacing a hydrogen atom at carbon 10, limonen-10-ol was not expected to be bactericidal and fungicidal. It should be noted in the structures of the monocyclic monoterpenes that follow, that none of the monocyclic monoterpenes that are known to be bactericidal, have an oxygen atom or a hydroxyl group at carbon 9 or 10 as can be appreciated in the structures of: perillyl alcohol, carveol, carvone, dihydrocarveol, dihydrocarvone pulegone, isopulegol, menthol, menthone, terpinen-4-ol, and a-terpineol which follow.

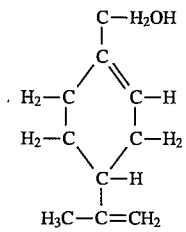

Perillyl Alcohol

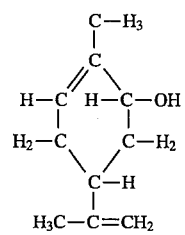

Carveol

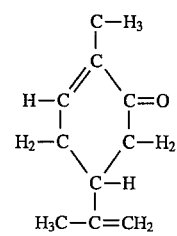

Carvone

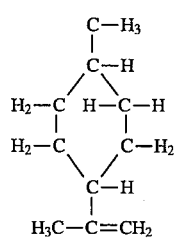

Dihydrocarveol

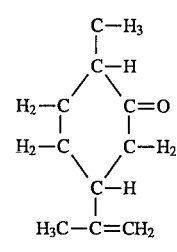

Dihydrocarvone

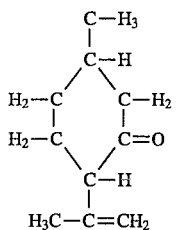

Pulegone

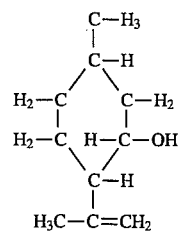

Isopulegol

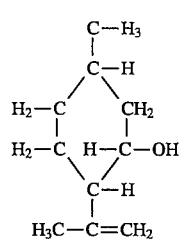

Menthol

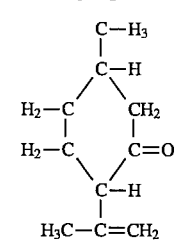

Menthone

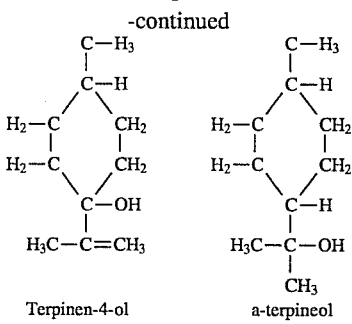

Terpinen-4-ol     a-terpineol

Limonen-10-ol is an oil with a fruity aroma that is soluble in alcohol and is miscible in oil. Although it is insoluble in water, it can be easily emulsified in water. It is poorly soluble in propylene glycol, and is almost insoluble in glycerine. Limonen-10-ol occurs naturally, but heretofore, it has not been used as a bactericide nor fungicide.

Limonen-10-ol is available commercially from the Aldrich Chemical Company, 940 Saint Paul Avenue, Milwaukee, Wis. 53233, catalogue number 21,841-3, and from George Majetich PhD, Department of Chemistry, University of Georgia, Athens, Ga. 30602. It is produced by a proprietary method of oxygenating d-limonene.

(2) Description of the Prior Art

Zuckerman studied the effect of auto-oxidized d-limonene on bacteria, and found it was weakly bacteriostatic, was unstable, and lost its bacteriostatic effect on keeping as was discussed in Nature 168:517 (1961). He never studied limonen-10-ol. Kurita investigated the fungicidal activity of several components of essential oils as was reported in Biol. Chem., 45(4), 945-952, 1981, but he never studied the antimicrobial activity of limonen-10-ol against bacteria, yeast nor fungi. Murdock and Allen showed the germicidal effect of sodium benzoate against yeast was enhanced by orange peel oil and d-limonene, as was outlined in Food Technology Vol 14, No 9, 1960, pages 441–5. They never studied the activity of limonen-10-ol against bacteria, yeast nor fungi. Kellner et al demonstrated that ethereal oils and some of their components have anti-bacterial activity as was reported in Arneimittel-Forechung, 5, 224-9, 1955. He confirmed that limonene is not bactericidal. He never studied limonen-10-ol for bactericidal nor fungicidal activity. Gauvreau showed a means of producing disinfecting compositions in U.S. Pat. No. 3,595,975 by combining cetyl pyridinium with terpenes to form antiseptics, but he never studied limonen-10-ol alone nor in combination with cetyl pyridinium hydrochloride. A. Morel revealed the sterilizing action of carveol, dihydrocarveol, and their ozonization products in Comp. Rend. Soc. Biol. Volume 115, pages 536–8 (1934). He demonstrated the bactericidal effect of carveol and dihydrocarveol, but he never studied the bactericidal nor fungicidal activity of limonen-10-ol. The applicants discovered that limonene can be made bactericidal and fungicidal by oxidation as was outlined in U.S. Pat. Nos. 5,153,229 and 5,229,425 but limonen-10-ol was never studied for bactericidal nor fungicidal activity and limonene-10-ol has never been identified in oxidized limonene.

It should be pointed out that drugs which are bactericidal are usually not fungicidal, and drugs which are fungicidal are usually not bactericidal. In addition, drugs which are bactericidal frequently promote the growth of yeast. Table A, which follows, exemplifies the bactericidal and fungicidal activity of several commonly used anti-bacterial, anti-yeast, and anti-fungal antibiotics.

TABLE A

| ANTIBIOTICS | ANTIBIOTIC ACTIVITY AGAINST | | | | |
|---|---|---|---|---|---|
| | $Gm^+$ Bac | $Gm^-$ Bac | AFBact | Yeast | Fungi |
| A. ANTIBACTERIAL | | | | | |
| 1. Ampicillin | YES | YES | NO | NO | NO |
| 2. Cephalothin | YES | YES | NO | NO | NO |
| 3. Chloramphenicol | YES | YES | NO | NO | NO |
| 4. Erythromycin | YES | NO | NO | NO | NO |
| 5. Ethambutol | NO | NO | YES | NO | NO |
| 6. Gentamicin | YES | YES | NO | NO | NO |
| 7. Isoniazid | NO | NO | YES | NO | NO |
| 8. Nitrofurantoin | NO | YES | NO | NO | NO |
| 9. Penicillin | YES | NO | NO | NO | NO |
| 10. Rifampin | YES | NO | YES | NO | NO |
| 11. Streptomycin | YES | YES | YES | NO | NO |
| 12. Sulfonamides | NO | YES | NO | NO | NO |
| 13. Tetracycline | YES | YES | NO | NO | NO |
| 14. Vancomycin | YES | YES | NO | NO | NO |
| B. ANTIYEAST | | | | | |
| 1. Nystatin | NO | NO | NO | YES | NO |
| 2. Gentian violet | NO | NO | NO | YES | NO |
| C. ANTIFUNGAL | | | | | |
| 1. Chlotrimazole | NO | NO | NO | YES | YES |
| 2. Griseofulvin | NO | NO | NO | NO | YES |

$Gm^+$ Bac = Gram Positive Bacteria, $Gm^-$ Bac = Gram Negative Bacteria, AFBac = Acid Fast Bacteria, YES = Kills Organism, NO = No Activity Against Organism It should be noted from the table above that none of the anti-bacterial antibiotics kill yeast nor fungi, and none of the anti-yeast nor anti-fungal antibiotics kill bacteria. Thus, an anti-fungal or anti-yeast antibiotic is not expected to kill bacteria and an anti-bacterial antibiotic is not expected to kill yeast nor fungi. Anti-fungal antibiotics do not necessarily kill yeast and anti-yeast antibiotics do not necessarily kill fungi.

DISCLOSURE OF THE INVENTION

This invention relates to the use of limonen-10-ol as an antimicrobial to kill bacteria, yeast, and fungi. Limonen-10-ol is an oil that is available commercially, but heretofore, it has not been recognized as an antimicrobial. It is slightly viscous and when applied, readily adheres to glass, metal, wood, cloth, rope, book covers, paper, paint, cement, ceramics, plastic, plant surfaces, skin, mucous membranes, and teeth leaving an oily film. Because it adheres to surfaces and is not soluble in water, it allows prolonged exposure and makes limonen-10-ol an ideal antimicrobial for treatment of infected plants, animals and humans, regardless of whether they are infected with bacteria, yeast, or fungi.

The exact method of killing bacteria, yeast, and fungi is unknown, but it is thought that limonen-10-ol kills bacteria, yeast, and fungi by lysing the cell membrane of the organisms which is lethal to the organisms.

In practice, any surface, on which it is desirable to kill or prevent the growth of bacteria, yeast or fungi, is treated with bactericidal, fungicidal, and/or effective concentrations of limonen-10-ol by swabbing, wiping, painting, washing, brushing, spraying, or any other direct application technique. Alternatively, limonen-10-ol can be incorporated in creams, ointments, tinctures, gels, suppositories, paints, sprays, sealers, aerosols, toothpastes, solutions, emulsions, soaps, scrubs, mouthwashes, or antiseptic, and applied anywhere it is desirable to kill or prevent the growth of bacteria, yeast, and fungi.

BEST MODE FOR CARRYING OUT THE INVENTION

The following examples are illustrative of the best mode of carrying out the invention. They are, obviously, not to be construed as limitative of the invention since various other embodiments can readily be evolved in view of the teachings provided herein.

EXAMPLE 1

ANTIMICROBIAL ACTIVITY OF LIMONEN 10-OL AGAINST BACTERIA, YEAST, AND FUNGI

The ANTIMICROBIAL contemplated by this invention is LIMONEN-10-OL which was studied for bactericidal, anti-yeast and fungicidal activity. The organisms tested included the bacteria: *Staphylococcus aureus* ATCC 25923, *Streptococcus mutans* which causes dental plaque, *Escherichera coli* 7, *Salmonella* 14 (para B), *Pseudomonas aeriginosa* 115, the yeast *Candida albicans*, a common cause of skin, mouth, and vaginal infections, and the fungi *Cladosporium cladosporides*, and *Auerobasidium pullans*. The bactericidal concentration, minimal effective concentration, and the fungitidal concentration of limonen-10-ol needed to kill these organisms are outlined in Table B below. The limonen-10-ol used in these tests was obtained from George Majetich PhD, Department of Chemistry, University of Georgia, Athens, Ga. 30602, was 99.9% pure by gas chromatography, and its structure was verified by NMR mass spectroscopy. Limonen-10-ol can be obtained from the Aldrich Chemical Company 940 West Saint Paul Avenue, Milwaukee, Wis. 53201; its catalogue number is 21,841-3.

TABLE B

BACTERICIDAL AND FUNGICIDAL ACTIVITY OF LIMONEN-10-OL

| ORGANISM | 10 Min | 60 Min | 24 Hrs |
|---|---|---|---|
| A. BACTERIA | MINIMAL BACTERICIDAL CONCENTRATION | | |
| 1. Staphylococcus aureus, ATCC 25923 | 0.06 | 0.01 | 0.005 |
| 2. Streptococcus mutans | 0.02 | 0.01 | 0.005 |
| 3. Escherichera coli 7 | 0.01 | 0.005 | 0.005 |
| 4. Salmonella 14 (para B) | 0.005 | 0.005 | 0.005 |
| 5. Pseudomonas aeruginosa ATCC 115 | 0.3 | 0.1 | 0.06 |
| B. YEAST | | | |
| 1. Candida albicans | 0.01 | 0.02 | 0.005 |
| C. FUNGI | MINIMUM FUNGICIDAL CONCENTRATION | | |
| 1. Cladosporium cladosporides OM489 | 0.01 | 0.02 | 0.005 |
| 2. Aureoblasidium pullans OM279C | 0.005 | 0.0025 | 0.0025 |

The standard assay used to test the bacterial activity of limonen-10-against the different strains of bacteria and yeast was as follows: various dilutions of limonen-10-ol were prepared in an appropriate broth medium for each test strain. An inoculum of $10^6$ colony-forming units (CFU)/ml was used. Each test was incubated at the proper temperature for each organism and subcultured (0.01 ml) at 10 minutes, 60 minutes, and 24 hours onto agar media free of limonen-10-ol. Results were expressed as the bactericidal concentration or the minimum effective concentration, i.e. the lowest concentration of limonen-10-ol (ml. limonen-10-ol/total ml of test) killing at least 99.99% of the bacterial or yeast inoculum.

The standard assay used to test the activity of limonen-10-ol against fungi was as follows: various dilutions of limonen-10-ol were prepared in Sabouraud dextrose broth medium. An inoculum of $10^6$ colony-forming units (CFU/ml) of fungi was introduced into each test, after which it was incubated at 37° C. in air, and subcultured (0.01 ml) at 10 minutes, 60 minutes, and 24 hours onto agar media free of limonen-10-ol. Results were expressed as the minimal fungicidal concentration, i.e. the lowest concentration of limonen-10-ol (ml limen-10-ol/total ml test), with no detectable viable colonies following subculture onto media free of limen-10-ol.

TABLE C

Test conditions used to assay the bactericidal activity of limonen-10-ol:

| ORGANISM | BROTH MEDIUM | SUBCULTURE AGAR MEDIUM | INCUBATION CONDITIONS |
|---|---|---|---|
| 1. Staphylococcus, Enterobacteriacea, and Pseudomonas | Mueller-Hinton | 5% sheep blood | Air @ 37° C. |
| 2. Streptococcus | Todd-Hewitt | 5% sheep blood | 10% $CO_2$ in air at 37° C. |
| 3. Yeast | Sabouraud dextrose | 5% sheep blood | air at 37° C. |
| 4. Fungi | Sabouraud dextrose with 0.05% yeast extract | | air at 37° C. |

EXAMPLE 2

FORMULATIONS WHICH INCORPORATE LIMONEN-10-OL AS THE ANTIMICROBIAL COMPOUND TO KILL BACTERIA, YEAST, AND FUNGI

The following formulations are prepared using limonen-10-ol in liquids, gels, soaps, pastes, creams, ointments, suppositories, tampons, aerosols, paints, and emulsions. When bacteria, yeast, and fungi are treated with limonen-10-ol containing formulations, the formulations kill or prevent the growth of bacteria, yeast, and fungi.

A. LIQUIDS

1. Solutions or Sprays

| | CHEMICAL | % OF TOTAL | RANGE | ACTION |
|---|---|---|---|---|
| a. | Limonen-10-ol | 5.0% | 0.1–50% | fungicide |
| | Corn Oil | 95.0% | 50–99.9% | diluent |
| | | 100.0% | | |
| b. | Limonen-10-ol | 1.0% | 0.1–50% | bactericide |
| | Ethyl Alcohol | 99.0% | 50–99.9% | diluent |
| | | 100.0% | | |

2. Mouthwash

| | CHEMICAL | % OF TOTAL | RANGE | ACTION |
|---|---|---|---|---|
| a. | Limonen-10-ol | 5.0% | 0.1–50% | anti-yeast |
| | Flavor | 2.0% | 1–5% | flavor |
| | Ethyl Alcohol | 48.0% | 45–98.9% | diluent |
| | | 100.0% | | |

B. DENTIFRICE

1. Liquid

| CHEMICAL | % OF TOTAL | RANGE | ACTION |
|---|---|---|---|
| Liquid soap concentrate | 5.0% | 2–10% | surfactant |
| Saccharin | 0.2% | 0.1–1.0% | flavor |
| Clove Oil | 1.0% | 0.5–3.0% | flavor |
| Cinnamon Oil | 0.5% | 0.5–3.0% | flavor |
| Peppermint Oil | 0.5% | 0.5–3.0% | flavor |
| Ethyl Alcohol | 42.6% | 29.5–95.3% | diluent |
| Color | 0.2% | 0.1–0.5% | color |
| Limonen-10-ol | 50.0% | 1–50% | bactericide |
| | 100.0% | | |

2. Gel

| CHEMICAL | % OF TOTAL | RANGE | ACTION |
|---|---|---|---|
| Sodium monofluorophosphate | 0.8% | 0.5–1.5% | anti-plaque |
| Limonen-10-ol | 50.0% | 1–50% | bactericide |
| Hydrated silica xerogel | 10.0% | 8–15% | abrasive |
| Hydrated thickening silica | 8.5% | 5–10% | binder |
| Sorbitol 70% solution | 18.8% | 5–73.3% | humectant |
| Polyethylene glycol 32 | 5.0% | 3–7% | bodying agent |
| Sodium lauryl sulfate | 1.5% | 1–2% | surfactant |
| Carboxymethyl cellulose gum | 1.0% | 0.5–2% | binder |
| S D alcohol | 1.0% | 0.5–2% | stabilizer |
| Flavor | 3.0% | 2–4% | flavor |
| Saccharin | 0.2% | 0.1–0.5% | flavor |
| F D & C Green #3 | 0.1% | 0.1–0.5% | color |
| F D & C Yellow #10 | 0.1% | 0.1–0.5% | color |
| | 100.0% | | |

3. Paste

| CHEMICAL | % OF TOTAL | RANGE | ACTION |
|---|---|---|---|
| Sodium monofluorophosphate | 0.8% | 0.5–1.5% | anti-plaque |
| Limonen-10-ol | 50.0% | 1–50% | bactericide |
| Dicalcium phosphate dihydrate | 22.0% | 20.4–30% | abrasive |
| Water | 16.0% | 11.1–69.5% | diluent |
| Glycerine | 5.1% | 4.5–12.5% | bodying agent |
| Flavor | 2.0% | 2–3% | flavor |
| Sodium lauryl sulfate | 1.5% | 1–2% | surfactant |
| Carboxymethyl | 1.4% | 0.5–2.0% | binder |

C. OINTMENTS & SUPPOSITORIES WITH AND WITHOUT HYDROCORTISONE (continued)

| CHEMICAL | % OF TOTAL | RANGE | ACTION |
|---|---|---|---|
| cellulose gum Tetrasodium pyrophosphate | 1.0% | 0.5–2.0% | binder |
| Sodium saccharin | 0.2% | 0.1–0.5% | flavor |
| | 100.0% | | |

1. Ointment With Hydrocortisone

| CHEMICAL | % OF TOTAL | RANGE | ACTION |
|---|---|---|---|
| Limonen-10-ol | 1.0% | 0.1–15.0% | bactericide |
| Polyethylene glycol 3350 | 59.5% | 48.5–59.7% | bodying agent & emulsifier |
| Polyethylene glycol 400 | 39.5% | 31.5–39.7% | bodying agent & emulsifier |
| Hydrocortisone | 1.0% | 0.5–5.0% | anti-inflammatory |
| | 100.0% | | |

2. Ointment Without Hydrocortisone

| CHEMICAL | % OF TOTAL | RANGE | ACTION |
|---|---|---|---|
| Limonen-10-ol | 1.0% | 0.1–15.0% | anti-yeast |
| Polyethylene glycol 3350 | 59.5 | 51.0–59.95% | bodying agent & emulsifier |
| Polyethylene glycol 400 | 39.5% | 34.0–39.95% | bodying agent & emulsifier |
| | 100.0% | | |

3. Suppository Without Hydrocortisone

| CHEMICAL | % OF TOTAL | RANGE | ACTION |
|---|---|---|---|
| Limonen-10-ol | 1.0% | 0.1–15.0% | fungicide |
| Polyethylene glycol 1000 | 9.5% | 51.0–59.95% | bodying agent & emulsifier |
| Polyethylene glycol 3350 | 39.5% | 34.0–39.95% | bodying agent & emulsifier |
| | 100.0% | | |

4. Suppository With Hydrocortisone

| CHEMICAL | % OF TOTAL | RANGE | ACTION |
|---|---|---|---|
| Limonen-10-ol | 1.0% | 0.1–15.0% | anti-yeast |
| Polyethylene glycol 1000 | 74.0% | 60.0–75.2% | bodying agent & emulsifier |
| Polyethylene glycol 3350 | 24.0% | 20.0–24.2% | bodying agent & emulsifier |
| Hydrocortisone | 1.0% | 0.5–5.0% | anti-inflammatory |
| | 100.0% | | |

D. Creams Without Hydorcortisone

| CHEMICAL | % OF TOTAL | RANGE | ACTION |
|---|---|---|---|
| Limonen-10-ol | 1.0% | 0.1–15.0% | bactericide |
| Cetyl alcohol | 15.0% | 12.0–18.0% | thickener |
| Arlacel 165 | 5.0% | 3.5–7.5% | emulsifier |
| Sorbitol 70% solution | 5.0% | 3.5–8.0% | humectant |
| Water | 74.5% | 51.5–80.9% | diluent |
| | 100.0% | | |

| CHEMICAL | % OF TOTAL | RANGE | ACTION |
|---|---|---|---|
| Limonen-10-ol | 1.0% | 0.1–15.0% | anti-yeast |
| Spermaceti wax Sorbitan monostearate | 12.5% | 10.0–15.0% | thickener |
| Polyethylene 20 | 10.0% | 7.5–12.5% | emulsifier |
| Sorbitan monostearate | 6.0% | 4.0–8.0% | emulsifier |
| Water | 75.5% | 49.5–78.4% | diluent |
| | 100.0% | | |

E. CREAMS WITH HYDROCORTISONE

| CHEMICAL | % OF TOTAL | RANGE | ACTION |
|---|---|---|---|
| Limonen-10-ol | 1.0% | 0.1–15.0% | anti-yeast |
| Cetyl alcohol | 15.0% | 12.0–18.0% | thickener |
| Arlacel 165** | 5.0% | 3.5–7.5% | emulsifier |
| Sorbitol 70% solution | 5.0% | 3.5–8.0% | humectant |
| Hydrocortisone | 1.0% | 0.5–5.0% | anti-inflammatory |
| Water | 73.0% | 46.5–80.4% | diluent |
| | 100.0% | | |

*Croda, Inc., 51 Madison Ave., New York, New York 10010
**Glycerol monostearate and polyoxyethylene stearate ICI of America (Formerly Atlas Chemical Industries), Wilmington, Delaware 19899

F. TAMPONS

| CHEMICAL | % OF TOTAL | RANGE | ACTION |
|---|---|---|---|
| Limonen-10-ol (2cc) 2Gm | 8.0% | 1–15% | bactericide |

-continued

| CHEMICAL | % OF TOTAL | RANGE | ACTION |
|---|---|---|---|
| Tampon 23Gm | 92.0% | 85–99% | reservoir for bactericide |
| | 100.0% | | |

G. AERSOLS WITHOUT HYDROCORTISONE

| CHEMICAL | % OF TOTAL | RANGE | ACTION |
|---|---|---|---|
| Limonen-10-ol | 5.0% | 0.5–50% | fungicide |
| Ethyl alcohol | 95.0% | 50–99.5% | diluent |
| | 100.0% | | |

Pressurized nitrogen propellant at 100–125 psig

| CHEMICAL | % OF TOTAL | RANGE | ACTION |
|---|---|---|---|
| Limonen-10-ol | 10.0% | 0.5–50.0% | anti-yeast |
| Soybean Oil | 90.0% | 50.0–99.5% | diluent |
| | 100.0% | | |

Pressurized nitrogen propellant at 100–125 psig

H. AERSOL WITH HYDROCORTISONE

| CHEMICAL | % OF TOTAL | RANGE | ACTION |
|---|---|---|---|
| Limonen-10-ol | 10.0% | 0.5–50.0% | bactericide |
| Soybean oil | 98.0% | 45–99.0% | diluent |
| Hydrocortisone | 1.0% | 0.5–5.0% | anti-inflammatory |
| | 100.0% | | |

Pressurized nitrogen propellant at 100–125 psig

I. OIL IN WATER EMULSION

| CHEMICAL | % OF TOTAL | RANGE | ACTION |
|---|---|---|---|
| (1) Limonen-10-ol | 0.1% | 0.1–50% | fungicide |
| (2) Corn oil | 10.0% | 10–15% | oil |
| (2) Arlacel 40** | 2.0% | 1–3% | emulsifier |
| (2) Tween 40 | 3.0% | 2–4% | emulsifier |
| (3) Water | 84.9% | 28–86.9% | diluent |
| | 100.0% | | |

Heat (2) to 70° C. Heat (3) to 72° C. Add (3) to (2) with continuous agitation. When (3) and (2) cool to 40° C., add (1) with continuous agitation until room temperature is reached.

J. OIL IN WATER EMULSION WITH SOAP (FUNGICIDAL OR BACTERICIDAL SOAP)

| CHEMICAL | % OF TOTAL | RANGE | ACTION |
|---|---|---|---|
| (1) Limonen-10-ol | 1.0% | 0.1–25% | bactericide |
| (2) Corn oil | 30.0% | 20.0–40.0% | oil |
| (2) Arlacel 40** | 2.0% | 1.0–3.0% | emulsifier |
| (2) Tween 40 | 3.0% | 2.0–4.0% | emulsifier |
| (2) Liquid soap concentrate | 3.5% | 2.5–5.0% | surfactant |
| (3) Water | 60.5% | 23–74.4% | diluent |
| | 100.0% | | |

Heat (2) to 70° C. Heat (3) to 72° C. Add (3) to (2) with continuous agitation. When (3) and (2) cool to 40° C., add (1) with continuous agitation until room temperature is reached.

K. WATER IN OIL EMULSION

| CHEMICAL | % OF TOTAL | RANGE | ACTION |
|---|---|---|---|
| (1) Limonen-10-ol | 1.0% | 0.1–25% | anti-yeast |
| (2) Arlacel 186** | 3.0% | 2.0–4.0% | emulsifier |
| (2) Soybean oil | 15.0% | 10.0–25.0% | oil |
| (2) Ceresin wax | 0.5% | 0.3–0.6% | thickener |
| (2) Beeswax | 0.5% | 0.3–0.6% | thickener |
| (2) Tween 80 | 0.5% | 0.3–0.6% | emulsifier |
| (3) Water | 79.5% | 44.2–87.0% | diluent |
| | 100.0% | | |

Heat (2) to 70° C. Heat (3) to 72° C. Add (3) to (2) with continuous agitation. When (3) and (2) cool to 40° C., add (1) with continuous agitation until room temperature is reached.

L. PAINT

1. Enamel

| CHEMICAL | % OF TOTAL | RANGE | ACTION |
|---|---|---|---|
| Limonen-10-ol | 1.00% | 1–10% | bactericide |
| Titanium dioxide | 14.91% | 12–16% | pigment |
| Calcium carbonate | 29.83% | 25–35% | pigment |
| Silicate | 4.81% | 3–6% | pigment |
| Soya alkyd resin | 25.72% | 22–28% | pigment (binder) |
| Mineral spirits | 23.73% | 5–37% | solvent (thinner) |
| | 100.00% | | |

2. Latex

| CHEMICAL | % OF TOTAL | RANGE | ACTION |
|---|---|---|---|
| Limonen-10-ol | 1.0% | 1–10% | fungicide |
| Titanium dioxide | 10.76% | 8–12% | pigment |
| Silicate | 12.91% | 10–16% | pigment |
| Calcium carbonate | 20.91% | 15–25% | pigment |
| Vinyl acrylic resin solids | 12.22% | 10–16% | vehicle (binder) |
| Glycol | 8.30% | 6–10% | solvent (thinner) |
| Water | 34.00% | 12–50% | solvent (thinner) |
| | 100.00% | | |

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A method of killing bacteria, fungi or yeast comprising treating bacteria, fungi or yeast in their habitat with lethal concentrations of limonen-10-ol.

2. The method of claim 1 wherein said bacteria are selected from a group consisting of Staphylococcus, Enterobacteriaceae, and Streptococcus.

3. The method of claim 1 wherein said fungi are selected from a group consisting of Aureoblasidium and Cladosporium.

4. A method of claim 1 for killing yeast wherein said yeast is *Candida albicans*.

* * * * *